United States Patent
Viladot Perice et al.

(10) Patent No.: US 8,398,691 B2
(45) Date of Patent: Mar. 19, 2013

(54) SURGICAL DEVICE FOR TREATING FLAT FEET, AND A CORRESPONDING SURGICAL KIT

(75) Inventors: Ramon Viladot Perice, Barcelona (ES); Greta Dereymaeker, Oud-Heverlee (BE); Patrice Francois Diebold, Nancy (FR); Beat Hintermann, Riehen (CH)

(73) Assignee: Newdeal S.A.S., Lyons (FR)

( * ) Notice: Subject to any disclaimer, the term of this patent is extended or adjusted under 35 U.S.C. 154(b) by 1410 days.

(21) Appl. No.: 11/383,101

(22) Filed: May 12, 2006

(65) Prior Publication Data
US 2006/0293676 A1 Dec. 28, 2006

(30) Foreign Application Priority Data
May 13, 2005 (FR) ...................................... 05 04877

(51) Int. Cl.
*A61B 17/84* (2006.01)
(52) U.S. Cl. .................. 606/327; 606/326; 606/313
(58) Field of Classification Search .................. 606/311, 606/312, 314, 315, 316, 317, 318, 319, 320, 606/321, 313, 300, 301, 302, 303, 304, 305, 606/306, 307, 308, 309, 310; 409/285, 298, 409/276, 280, 282; 411/451.1, 455, 456, 411/451.3, 511; 403/72–74, 285, 298, 276, 403/280, 282
See application file for complete search history.

(56) References Cited

U.S. PATENT DOCUMENTS

| | | | | |
|---|---|---|---|---|
| 1,354,549 A * | 10/1920 | Gilmer | ......................... | 403/280 |
| 3,764,446 A * | 10/1973 | Martin | ............................. | 428/52 |
| 4,297,063 A * | 10/1981 | Hart | .............................. | 411/199 |
| 5,232,451 A * | 8/1993 | Freitas et al. | ................. | 604/174 |
| 5,360,450 A * | 11/1994 | Giannini | .................... | 623/21.19 |
| 5,370,646 A * | 12/1994 | Reese et al. | .................. | 606/324 |
| 5,460,468 A * | 10/1995 | DiStacio | ...................... | 411/329 |
| 5,935,169 A * | 8/1999 | Chan | ........................... | 623/23.48 |
| 5,957,953 A * | 9/1999 | DiPoto et al. | ................. | 606/232 |
| 6,136,032 A | 10/2000 | Viladot Perice et al. | | |
| 6,942,666 B2 * | 9/2005 | Overaker et al. | ............. | 606/232 |
| 7,189,044 B2 * | 3/2007 | Ball | .............................. | 411/329 |
| 2002/0133159 A1 * | 9/2002 | Jackson | ......................... | 606/73 |
| 2002/0168244 A1 * | 11/2002 | DiStasio et al. | ............... | 411/299 |
| 2004/0039383 A1 * | 2/2004 | Jackson | .......................... | 606/61 |
| 2005/0070901 A1 * | 3/2005 | David | ............................. | 606/61 |
| 2005/0277924 A1 * | 12/2005 | Roychowdhury | .............. | 606/61 |

FOREIGN PATENT DOCUMENTS
EP 0 560 249 A 9/1993
* cited by examiner

*Primary Examiner* — Jan Christopher Merene
(74) *Attorney, Agent, or Firm* — Jason A. Bernstein; Barnes & Thornburg LLP

(57) ABSTRACT

A surgical device for treating the pathology of flat feet, the device comprising an outer casing; and an expansion member suitable for moving inside said outer casing in a compression direction, for causing said outer casing to expand radially; the surgical device being provided with non-return check means shaped to allow the expansion member to move in the compression direction towards an operating position inside the outer casing and to oppose movement of the expansion member in the reverse direction once said operating position is reached, so as to prevent the expansion member from being expelled.

26 Claims, 2 Drawing Sheets

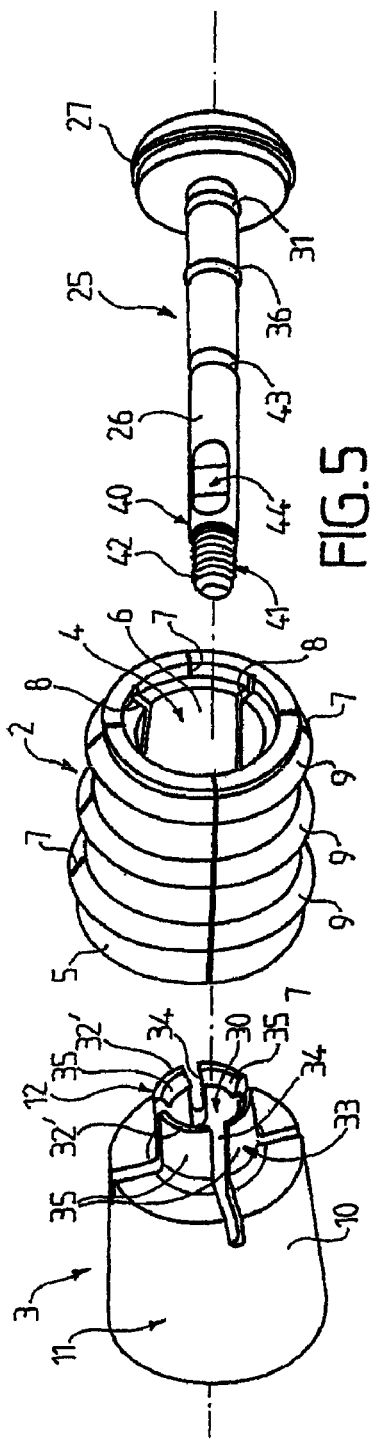

SURGICAL DEVICE FOR TREATING FLAT FEET, AND A CORRESPONDING SURGICAL KIT

PRIORITY CLAIM

This application is based upon and claims priority on French Patent Application No. FR-05 04877, having a Filing Date of May 13, 2005, which is hereby incorporated by reference in its entirety.

FIELD OF THE INVENTION

The present invention relates to the general technical field of surgical devices used for treating the pathology of "flat feet", in particular in children or in adults.

The present invention relates more particularly to a surgical device for treating the pathology of flat feet, said surgical device comprising at least the following two components:
an expansible outer casing; and
an expansion member suitable for moving in said outer casing in a compression direction, said outer casing and said expansion member being shaped so that moving the expansion member in the compression direction causes said outer casing to expand radially.

BACKGROUND OF THE INVENTION

The phenomenon of flat feet is very often due to misalignment of the ankle bone or "astragalus" and of the heel bone or "calcaneus", causing a deformation in the foot arch.

In order to remedy this type of pathology, it is known that an implant or "endorthesis" can be inserted into the tarsal sinus. That implant then acts as a wedge whose function is to re-align the calcaneus and the astragalus. When the re-alignment of the calcaneus and of the astragalus is satisfactory, i.e., in general, about nine months after being fitted, the implant is removed by being extracted with forceps.

In some known implants, an outer casing made of polyethylene is in the form of a cylinder through the center of which a tunnel is bored into which a screw is inserted. The outer casing is provided with notches enabling it to expand under the effect of the advancing screw. By expanding, the implant opens the canal of the tarsal sinus so as to reposition the astragalus on the calcaneus.

The major drawback of that type of implant is that, in its expanded configuration, it does not have a shape that is complementary to the shape of the cavity of the tarsal sinus.

In order to mitigate that drawback, another surgical device has been developed that is made up of three components, namely:
a central body provided with an external thread, with a head for blocking movement in translation;
an expansion cone provided with an internal thread, suitable for co-operating with the external thread on the central body; and
an outer ring that can be expanded under the effect of the expansion cone moving in said outer ring while the central body is being tightened.

Such devices generally give good results. In particular, such devices can, by means of their particular shapes, be locked easily in the cavity of the tarsal sinus. However, those devices also suffer from non-negligible drawbacks.

In particular, the system of assembly by screw-fastening, which offers the advantage of being reversible and thus of facilitating early extraction of the implant by reducing its diameter, by loosening the expansion cone, suffers from the fact that the expansion can loosen spontaneously, while the device is implanted. In which case, the effectiveness of the implant is reduced, since said implant is no longer capable of acting as a wedge.

SUMMARY OF THE INVENTION

The features of the present invention are thus to remedy the various above-mentioned drawbacks, and to propose a novel surgical device for treating the pathology of "flat feet", and that presents reliability that is improved relative to the reliability of prior devices.

Another feature of the invention is to propose a novel surgical device that is easy to insert and then to lock in position in the cavity of the tarsal sinus.

Another feature of the invention is to propose a novel surgical device whose expanded configuration is particularly well suited to the geometrical shape of the cavity of the tarsal sinus.

Features assigned to the invention are also to propose a novel surgical kit for treating the pathology of flat feet that makes it possible to implant a surgical device in the cavity of the tarsal sinus in precise and reliable manner.

Another feature of the invention is to propose a novel surgical kit for treating the pathology of flat feet that is particularly easy for the surgeon to manipulate.

Features assigned to the invention are also to propose a novel surgical method of treating the pathology of flat feet that makes it possible, by means of an implantable surgical device, to realign the calcaneus and the astragalus, with improved reliability relative to the reliability of prior art methods.

The features assigned to the invention are achieved by means of a novel surgical device for treating the pathology of flat feet, said surgical device comprising at least two components:
an expansible outer casing; and
an expansion member suitable for moving inside said outer casing in a compression direction, said outer casing and said expansion member being shaped so that moving the expansion member in the compression direction causes said outer casing to expand radially;
said surgical device being provided with non-return check means shaped to allow the expansion member to move in the compression direction towards an operating position inside the outer casing, and to oppose movement of the expansion member in the reverse direction once said operating position is reached, so as to prevent the expansion member from being expelled.

The features assigned to the invention are also achieved by means of a novel surgical kit for treating the pathology of flat feet, said surgical kit comprising:
a surgical device as defined above, including graspable means; and
a fitting instrument suitable for being connected mechanically to the graspable means and for exerting a traction force on said graspable means, while also pushing the expansion member away in the compression direction so that said expansion member penetrates progressively into the outer casing while causing said outer casing to expand.

The features assigned to the invention are also achieved by means of a novel surgical method of treating the pathology of flat feet, said surgical method comprising:
an implantation step consisting in inserting a surgical device having an expansible outer casing into the tarsal sinus of the foot; and an expansion step consisting in inserting an expansion member into the outer casing and in moving it therein so as to cause said outer casing to expand;

said method further comprising a locking step consisting in using non-return check means to prevent the expansion member from being expelled from the outer casing once it has reached its operating position inside said outer casing.

BRIEF DESCRIPTION OF THE DRAWINGS

Other features and advantages of the invention appear in more detail on reading the following description and on examining the accompanying drawings, which are given merely by way of non-limiting illustration, and in which:

FIG. 5 is an exploded perspective view of the components forming the surgical device shown in FIGS. 1 to 4;

FIG. 6 is a side view partially in section showing the surgical kit of the invention for treating the pathology of flat feet;

FIG. 7 is a section view of a variant embodiment of a surgical device of the invention, in a configuration preceding diametrical expansion of said device;

FIG. 8 is a section view of the surgical device shown in FIG. 7, in its expanded, operating configuration; and FIG. 8a is a section view of a detail of the check means of the surgical device shown in FIG. 8.

DESCRIPTION OF THE INVENTION

Figure 1:
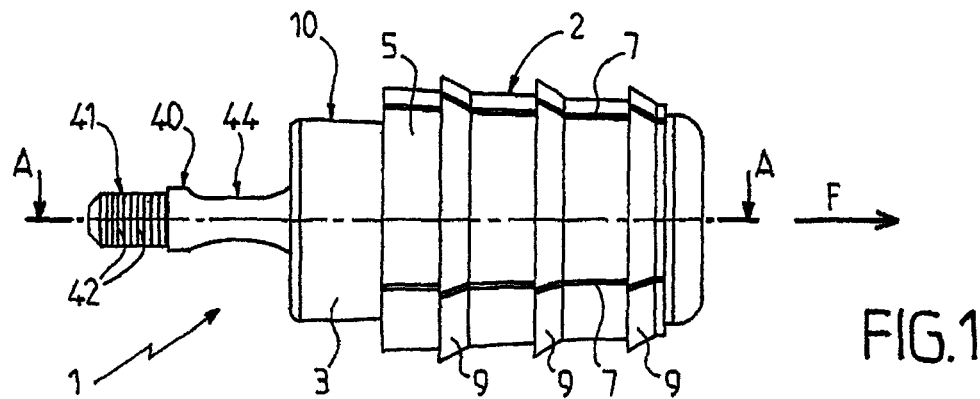
FIG. 1 is a profile view of a surgical device of the invention for treating the pathology of flat feet, in a pre-assembly position prior to it being expanded radially.

FIG. 1 shows a surgical device 1 for treating the pathology of flat feet, before it is mounted in the cavity of the tarsal sinus.

As shown in FIG. 1, the surgical device 1 comprises at least two components: an expansible outer casing 2 and an expansion member 3. Advantageously, the expansion member 3 is in the general shape of a truncated cone extending longitudinally along a longitudinal axis X-X' between a proximal end 3A and a distal end 3B.

The expansion member 3 is suitable for moving inside the outer casing 2 in a compression direction F that is preferably parallel to the longitudinal axis X-X', the outer casing 2 and the expansion member 3 being shaped so that the expansion member 3 moving in the compression direction F causes the outer casing 2 to expand radially.

The outer casing 2 is advantageously in the form of a ring of conical shape whose main axis coincides with the longitudinal axis X-X'. The outer casing 2 is preferably made of a biocompatible deformable material, e.g. metal or polyethylene.

Advantageously, the outer casing 2 defines an internal recess 4 into which the expansion 3 member engages. The outer casing 2 advantageously has an outside surface 5 serving, while the surgical device 1 is expanding, to come into abutment against the wall of the cavity of the tarsal sinus. The outer casing 2 also has an inside surface 6 defining the internal recess 4.

In order to enable the outer casing 2 to expand diametrically, said outer casing is provided with notches 7 disposed on the outside surface 5, and with notches 8 disposed on the inside surface 6. Preferably, the outer casing 2 has four notches 7 distributed over its outside surface 5, and four notches 8 distributed over its inside surface 6, said notches 7, 8 preferably being offset angularly relative to one another so as to enable the outer casing 2 to expand diametrically. In particular, the notches 7 provided in the outside surface 5 are preferably offset by 45° relative to the notches 8 provided in the inside surface 6. The notches 7, 8 are preferably provided longitudinally, along the outer casing 2, and they are of depth preferably greater than one half of the thickness of the outer casing 2. Thus, while the expansion cone 3 is penetrating into the recess 4, the edges of the notches 7, 8 move apart, thereby enabling the outer casing 2 to be expanded diametrically. Preferably, the notches 7, 8 are also distributed uniformly over the perimeter of the outer casing 2 so as to enable the surgical device 1 to expand diametrically in uniform manner.

Figure 2:
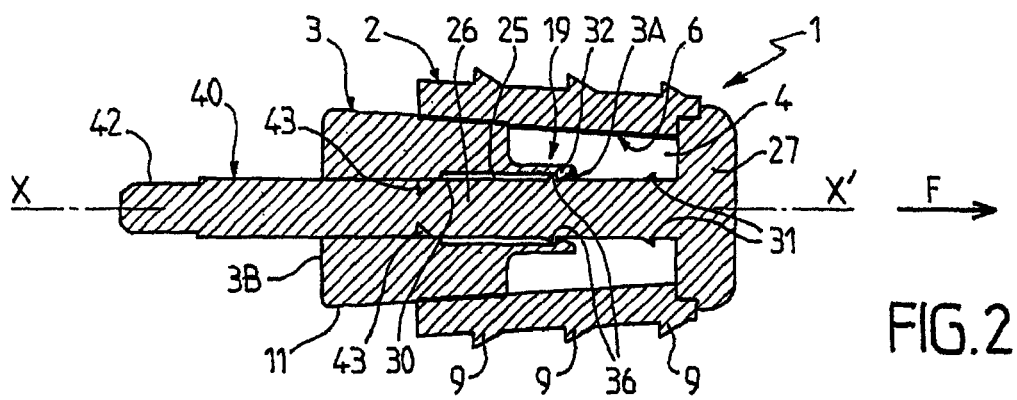
FIG. 2 is a section view on the line A-A shown in FIG. 1 of the surgical device shown in FIG. 1.

Preferably, and as is shown in FIGS. 1, 2, and 5, the outer casing 2 is provided with fins 9 over its outside surface 5, serving to oppose expulsion of the surgical device 1 after it has been put in place and caused to expand inside the cavity of the tarsal sinus. Thus, while the surgical device 1 is expanding, the fins 9 come into positive abutment against the wall of the cavity, thereby preventing the surgical device 1 from being expelled.

Advantageously, the expansion member 3 has an expansion cone 10 with an outside face 11 shaped so as to come into surface abutment against the outer casing 2, and preferably against the inside surface 6 of the outer casing 2, so as to cause said outer casing to expand progressively under the effect of the expansion cone 10 moving in the compression direction F.

Preferably, the expansion member 3, and in particular the expansion cone 10, is made of a biocompatible metal material, e.g. titanium or stainless steel.

Figures 4, 4A:
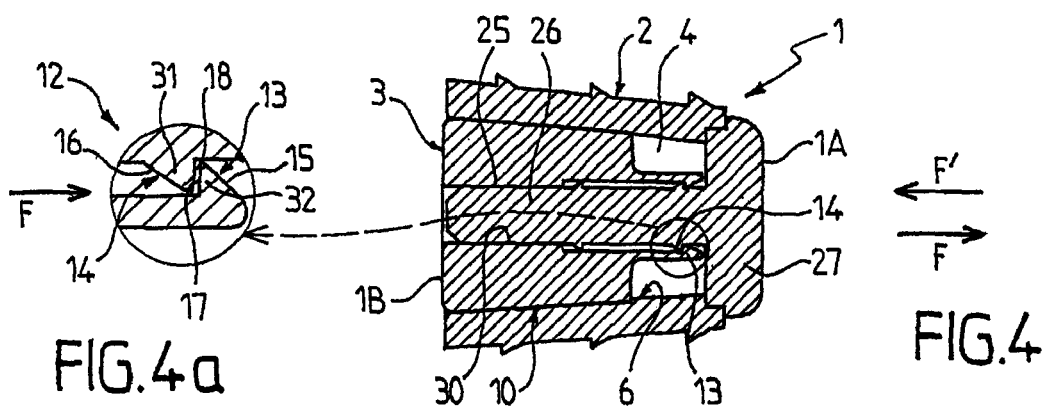
FIG. 4 is a section view of the surgical device shown in FIGS. 1, 2, and 3 in its expanded operating position, after the graspable means have been removed.
FIG. 4a is a section view of a detail of the non-return check means of the surgical device shown in FIG. 3.

The surgical device 1 extends between an proximal end 1A which, in the operating position shown in FIG. 4, is situated fully inserted into the cavity of the tarsal sinus, and a distal end 1B facing towards the outside of the cavity, opposite from the proximal end 1A. Advantageously, the smaller diameter of the expansion cone 10 is closer to the proximal end 1A of the surgical device 1, and its larger diameter is situated at the opposite end, closer to the distal end 1B of the surgical device 1.

Advantageously, the conical outside face 11 of the expansion cone 10 comes into abutment against the inside surface 6 of the internal recess 4, which is also conical in shape.

In order to enable the outer casing 2 to expand radially, the outside diameter of the expansion cone 10 is significantly larger than the corresponding inside diameter of the internal recess 4 when the outer casing 2 is at rest, i.e. in its non-expanded configuration.

According to an essential characteristic of the invention, the surgical device 1 has non-return check means 12 shaped to enable the expansion member 3 to move in the compression direction F, towards an operating position inside the outer casing 2, and for opposing movement of the expansion member 3 in the reverse direction once said operating position has been reached, so as to prevent the expansion member 3 from being expelled from the outer casing 2.

In particular, once, the expansion member 3 and the outer casing 2 are assembled together in the operating position, the check means 12 serve to prevent the components (or parts)

forming the surgical device 1 from separating progressively and in uncontrolled manner, by locking the expansion member 3 in its operating position, thereby making the expansion member 3 irreversibly mounted.

Advantageously, the check means 12 comprise first and second mutual engagement means 13, 14 which are preferably associated directly or indirectly respectively with the expansion member 3 and with the outer casing 2, and which are suitable for co-operating together to enable the expansion member 3 to move in one direction only, namely in the compression direction F, towards its operating position inside the outer casing 2.

The term "associated" refers to the fact that, while the surgical device 1 is expanding, the first mutual engagement means 13 and the expansion member 3 form a single assembly whose two parts cannot move relative to each other and that is suitable for moving as one piece for expanding the outer casing 2. Similarly, the second mutual engagement means 14 are "associated" directly or indirectly with the outer casing 2, i.e. they are either provided directly thereon, or connected indirectly, via an intermediate part, to the outer casing 2 so as to be held stationary relative to the outer casing 2 while the expansion member 3 is moving, and so as to form, with said outer casing 2, a single assembly whose two parts cannot move relative to each other.

Advantageously, at least one of the mutual engagement means 13 is shaped and arranged to retract so as to go past the other mutual engagement means 14 while the expansion member 34 is moving in the compression direction F, thereby forming retractable engagement means. The retractable engagement means can be associated either with the outer casing 2 or with the expansion member 3.

Preferably the retractable engagement means 13 are resilient, enabling them to retract relative to the complementary mutual engagement means 14. This resilience can be procured by resilient returns means of the spring type mechanically connected to the retractable engagement means 13 so that, when the mutual engagement means 14 come into abutment against the corresponding retractable engagement means 13, said retractable engagement means are pushed back against the return force exerted by the resilient return means.

Preferably, the retractable return means 13 are themselves resilient, by being intrinsically flexible.

As is shown in FIG. 4a, the first and second mutual engagement means 13, 14 have first and second engagement faces 15, 16 that extend slantingly relative to the compression direction F, and that are suitable for sliding against each other while the expansion member 3 is moving towards its operating position.

Preferably, the first and second mutual engagement means 13, 14 also have first and second stop faces 17, 18 suitable for coming into abutment with each other so as to prevent the expansion member 3 from moving backwards in an expulsion direction F' opposite from the compression direction F, once the operating position is reached.

Advantageously, the surgical device 1 is provided with preassembly means 19 shaped to assemble the expansion member 3 to the outer casing 2 directly or indirectly by clipping. The "preassembled" configuration makes it easier for the surgeon to fit the surgical device 1, since the surgeon then merely has to insert the surgical device 1, in its "preassembled" configuration, into the cavity in the tarsal sinus, and then to cause the outer casing 2 to expand by moving the expansion member 3 relative to said outer casing 2.

Embodiments of the invention are described below with reference to FIGS. 1 to 5 and to FIGS. 7 and 8.

In a first exemplary embodiment of the invention, shown in FIGS. 7 and 8, the surgical device 1 is made up of an outer casing 2 and of the expansion member 3, thereby forming a surgical device 1 having two components (or parts).

In this variant, the outer casing 2 extends between a proximal end 2A situated in the vicinity of the corresponding proximal end IA of the surgical device 1 and a distal end 2B situated at the opposite end. The surgical device 1 has a head 20 for blocking movement in translation, which head is disposed at the proximal end 2A of the outer casing 2A so as to close the internal recess 4. The blocking head 20 can be formed by a cap secured to or integral with the outer casing 2.

In this variant, the expansion member 3 is formed by the expansion cone 2 which is in form of a solid truncated cone. As shown in FIGS. 7, 8, and 8a, the second mutual engagement means 14 are situated on the inside surface 6 of the internal recess 4 so as to co-operate with the first mutual engagement means 13 situated on the outside face 11 of the expansion member 3. The outside face 11 and the inside surface 6 are substantially smooth except for the presence of pieces in relief formed by the mutual engagement means 13, 14.

Preferably, and as shown in FIG. 8a, the first mutual engagement means 13 are preferably formed by a circular lip 21, extending around the periphery of the expansion member 3 in a plane that is substantially perpendicular to the compression direction F. The circular lip 21 advantageously projects from the outside face 11 of the compression member 3. The second mutual engagement means 14 are preferably formed by a first circular groove 22 provided in the inside surface 6 of the outer casing 2, and of shape preferably complementary to the shape of the circular lip 21. Preferably, the circular lip 21 and the first circular groove 22 are triangular in cross-section.

In this variant, the preassembly means 19 are preferably formed by a circular lip 21 and at least a second circular groove 23, provided in the inside surface 6 of the outer casing 2, and situated upstream from the first circular groove 22, relative to the compression direction F, said circular lip 21 serving to co-operate with said circular groove 23 as shown in FIG. 7.

The surgical device 1 shown in FIGS. 7, 8, and 8a operates as follows.

By moving in the compression direction F, the expansion member 3 comes, via its outside face 11 and via the circular lip 21, into positive and compressive abutment against the inside surface 6 of the outer casing 2, thereby causing said outer casing to expand diametrically. Once the pre-assembled configuration, shown in FIG. 7, is reached, the circular lip 21 comes to be received in the second circular groove 23, thereby preventing the expansion member 3 from returning in the expulsion direction F'. In this preassembly position, the expansion member 3 can, however, be moved in the compression direction F until it reaches its operating position shown in FIG. 8, in which it is locked in position firstly by the check means 12, preventing it from moving in the expulsion direction F', and secondly by the blocking head 20, limiting its movement in translation in the compression direction F. In its operating position, the circular lip 21 comes to be received in the first circular groove 22 provided for this purpose, so that the first and second stop faces 17, 18 come into abutment against each other.

In a second exemplary embodiment of the invention, shown in FIGS. 1 to 5, the surgical device 1 includes a guide device 25 shaped to co-operate with the expansion member 3 so as to guide said expansion member in translation inside the outer casing 2. More precisely, the guide member 25 comprises a central rod 26 extending substantially at the center of the outer casing 2, along the longitudinal axis X-X', and the expansion member 3 is provided with a central passageway 30 enabling it to slide along said central rod 26. The surgical device 1 is then made up of 3 components, namely the expansion member 3, the outer casing 2, and the guide member 25.

According to a particularly advantageous characteristic of the invention, the guide member 25 further comprises a blocking head 27 suitable for limiting the movement in translation of the expansion member 3 in the compression direction F, by forming an abutment against said expansion member. The blocking head 27 and the check means 12 then co-operate to lock the expansion member 3 in its operating position.

Preferably, the guide member 25 is made of a biocompatible metal material, such as titanium or stainless steel.

In the second exemplary embodiment of the invention, the second mutual engagement means 14 are preferably situated on the periphery of the central rod 26 so as to co-operate with the first engagement means 13, situated on the surface of the central passageway 30. The second mutual engagement means 14 are then associated with the outer casing 2 indirectly, via the intermediate part formed by the guide member 25. The first engagement means 13 advantageously project into the central passageway 30, from the surface of said central passageway 30.

Even more preferably, and as shown in FIG. 4a, the check means 12, and in particular the first and second mutual engagement means 13, 14 are formed by at least a first lip 31, associated with the outer casing 2 and preferably situated on the periphery of the central rod 26 so as to form a circular lip, and at least one backing lip 32 associated with the expansion member 3, and more preferably disposed so as to project into the central passageway 30.

Figure 3:
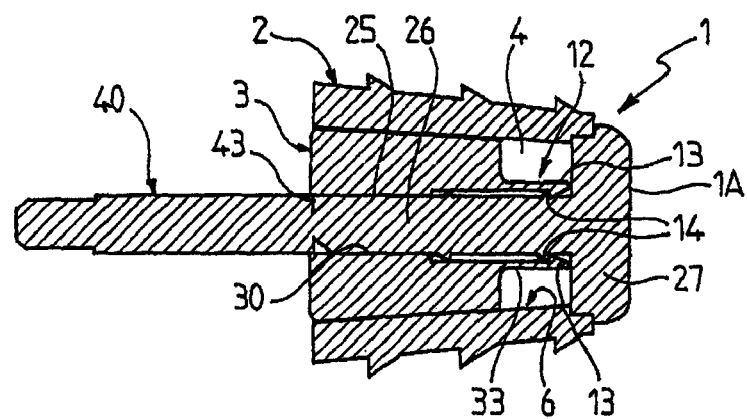
FIG. 3 is also a section view of the surgical device shown in FIGS. 1 and 2, in its expanded operating position, provided with graspable means for taking hold of it.

Advantageously, and as is shown in FIGS. 3 and 5, the expansion member 3 is extended towards the proximal end 1A of the surgical device 1 by a thin neck 33 surrounding the central passageway 30, the backing lip 32 being disposed around the neck 33 so as to project into the central passageway 30.

Particularly advantageously, and as shown in FIG. 5, slots 34 are provided along the neck 33 so as to define a plurality of flexible tongues 35 suitable for retracting in the manner of ratchets relative to the first lip 31 while the expansion member 3 is moving in the compression direction F. The backing lip 32 is thus made up of a plurality of backing lips 32' disposed on the flexible tongues 35, and advantageously forms snap-fastening in association with the first lip 31.

The periphery of the central rod 26 and the surface of the central passageway 30 are preferably substantially smooth, except for the presence of the mutual engagement means 13, 14 which form pieces in relief.

In this embodiment of the invention, the preassembly means 19 are preferably formed by the backing lip 32 and by at least a second lip 36 associated with the outer casing 2, and more precisely provided on the periphery of the central rod 26 and situated upstream from the first lip 31, relative to the compression direction F, said backing lip 32 serving to co-operate with said second lip 36 in the preassembly configuration shown in FIG. 2.

In a particularly advantageous characteristic of the invention, shown in FIGS. 1 to 3 and 5, the surgical device 1 has graspable means 40 serving to be connected mechanically to a fitting instrument 50 (FIG. 6) designed to clip together (or to snap-fasten together) the components making up the surgical device 1 by exerting a traction force on the graspable means 40, preferably in a direction opposite from the compression direction F. Preferably, the graspable means 40 include an end-piece 41 provided with an external thread 42 enabling it to be connected by screw-fastening to the fitting instrument 50 (FIG. 5).

The graspable means 40 are preferably formed by an extension to the central rod 26 that is situated at its end opposite from the blocking head 27. The graspable means 40 are also advantageously removable and preferably breakable so that they can be broken off. To this end, the central rod 26 and the graspable means 40 are advantageously made in one piece provided with a local narrow portion 43 defining a break zone at which the graspable means 40 can be separated from the central rod 26 when a traction force exceeding a threshold value is exerted on the graspable means 40.

Particularly advantageously, the break zone, and in particular the local narrow portion 43, is situated in the central passageway 30 of the expansion member 3 throughout expansion of the surgical device 1, thereby preventing the graspable means 40 from breaking prematurely, in particular by opposing bending and angular movement of the graspable member 40 relative to the longitudinal axis X-X' and relative to the central rod 26.

Breaking can take place only once the expansion member 3 has reached its operating position inside the outer casing 2, whereupon the break zone comes flush with the distal end 3B of the expansion member 3 so as to enable the graspable means 40 to be broken off, in particular by pulling on said graspable means and by inclining them relative to the longitudinal axis X-X' at the local narrow portion 43.

The surgical device 1 of the invention is advantageously dimensioned so that, when the expansion member 3 is in its operating position, the break zone (or the local narrow portion 43) is situated substantially at the distal end 3B of the expansion member 3, situated opposite from the blocking head 27.

Advantageously, the graspable means 40 are provided with a flat 44 serving to make it easier for the surgeon to take hold of it for unscrewing the end-piece 41 from the fitting instrument 50.

The present invention also relates to a surgical kit 100 for treating the pathology of flat feet, said kit comprising:

a surgical device 1 as described above, including graspable means 40; and a fitting instrument 50 suitable for being connected mechanically to the graspable means 40 and for exerting a traction force thereon, while pushing back the expansion member 3 in the compression direction F, so that said expansion member penetrates progressively into the outer casing 2, thereby causing said outer casing 2 expand, and in particular causing it to expand diametrically.

As shown in FIG. 6, the fitting instrument 50 comprises a main body 51 that is cylindrical in shape and that is provided with a cavity 52 in which a rod 53 is mounted. The rod 53 is mounted to move in translation in the cavity 52 and has a free end 53A on which the surgical device 1 is mounted. Said surgical device is, for example, screwed onto the free end 53A of the rod 53. the rod 53 is caused to move in the compression direction F by handles 54 and in particular by a stationary handle 55 secured to or integral with the main body 51, and a moving handle 56 mounted to pivot relative to the main body 51. The moving handle 56 extends between a free first end 56A and a second end 56B connected mechanically to the rod 53, so that pivoting the moving handle 56 causes a corresponding movement in translation of the rod 53, which slides in the main body 51. The fitting instrument 50 thus advantageously forms a pair of "rivet pliers".

Finally, the present invention relates to a surgical method of treating the pathology of flat feet, said method firstly including an implantation step, during which a surgical device 1 having an expansible outer casing 2 is inserted into the tarsal sinus of the foot. The surgical method of the invention then includes an expansion step, during which an expansion member 3 is inserted into the outer casing 2 and moved therein so as to cause said casing to expand.

According to an essential characteristic, the surgical method of the invention also includes a locking step during which, by using check means 12, the expansion member 3 is prevented from being expelled from the outer casing 2 once its operating position inside the outer casing 2 has been reached.

Particularly advantageously, prior to the expansion step, the method of the invention includes a preassembly first step, during which the expansion member 3 is assembled directly or indirectly, e.g. via an intermediate part, to the outer casing 2 so as to form an irreversibly-assembled single assembly. The preassembly step is advantageously performed by clipping, by preassembly means. This step is preferably performed on the site of manufacture of the surgical device 1, said surgical device preferably being sold in its preassembled configuration.

Advantageously, prior to the expansion step, the surgical method of the invention also includes a connection step, during which the surgical device 1 is connected mechanically to a fitting instrument 50 via graspable means 40 incorporated into the surgical device 1.

The expansion step then takes place by exerting traction on the graspable means 40, by means of the fitting instrument 50, so that the traction force exerted on the graspable means 40 causes the expansion member 3 to move in the outer casing 2, and causes said outer casing to expand diametrically. The expansion step continues until the expansion member is locked in position by the check means 12. According to a particularly advantageous characteristic of the invention, the locking step takes place by clipping or snap-fastening the expansion member 3 to the outer casing 2 directly or indirectly, i.e. via an intermediate part such as a guide member 25. In which case, the guide member 25 advantageously has a blocking head 27 which, in association with the check means 12, participates in locking the surgical device 1 by holding the expansion member 3 stationary between the blocking head 27 and the check means 12.

Particularly advantageously, the surgical method of the invention further includes a separation step, during which the graspable means 40 are separated from the surgical device 1, e.g. by being broken off, once the expansion step and the locking step have been performed.

The modes of operation and of use of the surgical device 1 and of the surgical kit 100 of the invention are described below with reference to FIGS. 1 to 6.

The surgical device 1 is inserted as follows. A single incision is made at the tarsal canal, and all of the components making up the surgical device of the invention are inserted in a preassembled configuration as shown in FIG. 2.

The surgical device 1 is connected to the fitting instrument 50 via the graspable means 40 which project on the outside of the surgical device 1. More precisely, the end-piece 41 of the graspable means 40 is preferably screwed to the free end 53A of the rod 53 of the fitting instrument 50.

Once the surgical device 1 is implanted, it is expanded and locked in the cavity of the tarsal sinus by pressing the handles 5, 56 together so as to exert a traction force on the graspable means 40 (and thus on the outer casing 2) via the rod 53, while pushing the expansion member 3 in the compression direction F via the end 51A of the main body 51, which end comes into abutment against the expansion member 3.

The expansion member 3, and in particular the expansion cone 10, then penetrates progressively into the internal recess 4 in the outer casing 2, and exerts outward compression thereon due to the difference between the diameter of the expansion cone 10 and the diameter of the internal recess 4. More precisely, as the outer casing 2 expands, the notches 7, 8 open progressively, and the fins 9 come into abutment against the cavity of the tarsal sinus, thereby locking the surgical device 1 inside said cavity.

The operating position of the expansion member 3 is reached when said expansion member comes into abutment against the blocking head 27, in particular via the neck 33 (FIG. 3) and/or when the first and second mutual engagement means 13, 14 snap-fasten with each other. The expansion member 3 is then locked in position, thereby irreversibly assembling the surgical device 1.

The surgeon can then cause the traction force to continue to be exerted on the graspable means 40 by pressing the handles 55, 56 together, while inclining the fitting instrument 50 so as to separate the graspable means 40 from the central rod 26 and more generally from the surgical device 1 by bending and traction breaking at the local narrow portion 43, the surgical device 1 then finding itself locked in position in the cavity of the tarsal sinus.

The present invention makes it easy for the surgical device 1 to be put in place and locked in the tarsal sinus, by means of a limited number of operations, while also offering good reliability, and in particular a limited risk of the surgical device 1 or of one of its components being expelled.

The invention claimed is:

1. A surgical device for treating the pathology of flat feet, comprising:
   an expansible outer casing having an inside surface;
   an expansion member having a central passageway and an outside face shaped so as to come into surface abutment against the outer casing inside surface, the expansion member being suitable for moving inside the outer casing in a compression direction, the outer casing and the expansion member being shaped so that moving the expansion member in the compression direction causes the outer casing to expand radially;
   a guide member comprising a central rod extending substantially at the center of the outer casing shaped to co-operate with the expansion member so as to guide said expansion member in translation inside the outer casing, the central rod being adapted to slide along the expansion member central passageway, the guide member further including a blocking head suitable for limiting movement in translation of the expansion member in the compression direction;
   a non-return check means disposed on the inside surface and the outside face, the check means comprising a first engagement means associated with the expansion member and second engagement means associated with the outer casing, the first and second engagement means have first and second engagement faces extending slantingly relative to the compression direction and adapted to slide axially against each other while the expansion member is moving towards its operating position, the check means being shaped to allow the expansion member to slidingly move in the compression direction towards an operating position inside the outer casing, and to irreversibly prevent axial sliding movement of the expansion member in the reverse direction once the operating position is reached, the check means and the blocking head being adapted to lock the expansion member in the operating position; and, a graspable member adapted to connect mechanically with a fitting instrument designed to clip together the components making up the surgical device by exerting a traction force on the graspable member, wherein the graspable member is formed by an extension to the central rod, at the end thereof that is situated opposite from the blocking head.

2. The device according to claim 1, wherein at least one of said mutual engagement means is shaped and arranged so as to retract in order to go past the other mutual engagement means while the expansion member is moving in the compression direction, thereby forming retractable engagement means.

3. The device according to claim 2, wherein the retractable engagement means are resilient.

4. The device according to claim 1, wherein the first and second mutual engagement means have first and second stop faces suitable for coming into abutment against each other so as to prevent the expansion member from moving back the other way once the operating position is reached.

5. The device according to claim 1, wherein the check means are formed by at least one first lip associated with the outer casing and by at least one backing lip associated with the expansion member.

6. The device according to claim 1, wherein the device being provided with preassembly means shaped to assemble the expansion member to the outer casing by clipping.

7. The device according to claim 5, wherein the device being provided with preassembly means shaped to assemble the expansion member to the outer casing by clipping, and the preassembly means being formed by the backing lip and by at least a second lip associated with the outer casing and situated upstream from the first lip relative to the compression direction, said backing lip serving to co-operate with said second lip.

8. The device according to claim 1, wherein the expansion member comprises an expansion cone, the outside face of the expansion cone coming into surface abutment against the outer casing so as to cause said outer casing to expand progressively under the effect of the expansion cone moving in the compression direction.

9. The device according to claim 1, wherein the device being constituted by the outer casing and by the expansion member, thereby forming a device made up of two components.

10. The device according to claim 9, wherein the outer casing defines an internal recess with an inside surface, and wherein the second engagement means are situated on said inside surface so as to co-operate with the first engagement means, situated on the outside face of the expansion member.

11. The device according to claim 1, wherein the blocking head is suitable for limiting movement in translation of the expansion member in the compression direction, the blocking head and the check means locking the expansion member in the operating position.

12. The device according to claim 1, wherein the second engagement means are situated on the periphery of the central rod, so as to co-operate with the first engagement means that project into the central passageway.

13. The device according to claim 12, wherein the check means are formed by at least one first lip associated with the outer casing and by at least one backing lip associated with the expansion member, and wherein the expansion member is extended by a thin neck surrounding the central passageway, the backing lip being disposed at said neck so as to project towards the inside of the central passageway.

14. The device according to claim 13, wherein slots are provided along the neck so as to define a plurality of flexible tongues suitable for retracting relative to the first lip while the expansion member is moving in the compression direction.

15. The device according to claim 1, wherein the graspable member is removable, by being suitable for being broken off.

16. The device according to claim 15, wherein a central rod and the graspable member are formed in one piece provided with a local narrow portion defining a break zone at which the graspable member is separated from the central rod when traction exceeding a threshold value is exerted on the graspable member.

17. The device according to claim 1, wherein the outer casing is provided with notches in its outside surface and in its inside surface, which notches are offset angularly so as to enable said outer casing to expand diametrically.

18. The device according to claim 1, wherein the outer casing is made of a biocompatible deformable material.

19. The device according to claim 1 wherein the outer casing is made of a biocompatible deformable material selected from the group consisting of metal and polyethylene.

20. A surgical kit for treating the pathology of flat feet, comprising:
a surgical device according to claim 1; and
a fitting instrument suitable for being connected mechanically to the graspable member and for exerting a traction force on said graspable member, while also pushing the expansion member away in the compression direction so that said expansion member penetrates progressively into the outer casing while causing said outer casing to expand.

21. A method of treating the pathology of flat feet, comprising:
an implantation step during which a surgical device according to claim 1 is inserted into the tarsal sinus of the foot;
an expansion step during which the expansion member is inserted into the outer casing and moved therein so as to cause said outer casing to expand; and,
a locking step during which, by using non-return check means, the expansion member is prevented from being expelled from the outer casing once the expansion member has reached its operating position inside said outer casing.

22. The method according to claim 21, further comprising, prior to the expansion step, a preassembly first step during which the expansion member is assembled to the outer casing in a manner such as to form an irreversibly-assembled single assembly.

23. The method according to claim 21, further comprising, prior to the expansion step, a connection step during which the surgical device is connected mechanically to a fitting instrument via graspable member incorporated into the surgical device.

24. The method according to claim 21, wherein the expansion step is performed by exerting traction on the graspable member by means of the fitting instrument so that the traction force exerted on the graspable means causes the expansion member to move into the outer casing and causes said outer casing to expand diametrically.

25. The method according to claim 21, further comprising a separation step during which the graspable member are separated from the surgical device once the expansion step and the locking step have been performed.

26. The method according to claim 21, wherein the locking step is performed by either clipping or snap-fastening the expansion member to the outer casing.

* * * * *